United States Patent [19]

Shields

[11] Patent Number: 5,044,376
[45] Date of Patent: Sep. 3, 1991

[54] VAGINAL DIAPHRAGMS WITH MEDICAMENT DISPENSING FOAM PADS

[76] Inventor: Jack W. Shields, 1950 Las Tunas Rd., Santa Barbara, Calif. 93103

[21] Appl. No.: 415,472

[22] Filed: Oct. 2, 1989

Related U.S. Application Data

[63] Continuation of Ser. No. 234,812, Aug. 22, 1988, abandoned.

[51] Int. Cl.$^5$ .............................................. A61F 6/10
[52] U.S. Cl. .................................. 128/837; 128/832; 128/841
[58] Field of Search ................. 128/832, 834, 837, 841

[56] References Cited

U.S. PATENT DOCUMENTS

| | | | |
|---|---|---|---|
| 2,020,107 | 11/1935 | Cruickshank | 128/832 X |
| 2,110,962 | 3/1938 | Munro | 128/832 X |
| 2,157,689 | 5/1939 | Clark, Jr. | 128/837 |
| 3,443,563 | 5/1969 | Ishihama et al. | 128/832 X |
| 3,683,904 | 8/1972 | Forster | 128/834 |
| 3,780,730 | 12/1973 | Weisman | 128/832 |
| 4,198,965 | 4/1980 | Strickman et al. | 128/832 |
| 4,219,016 | 8/1980 | Drobish et al. | 128/832 |
| 4,300,544 | 11/1981 | Rudel | 128/832 |
| 4,332,243 | 6/1982 | Gutnick | 128/832 X |
| 4,589,880 | 5/1986 | Dunn et al. | 128/832 |

FOREIGN PATENT DOCUMENTS

| | | | |
|---|---|---|---|
| 553547 | 6/1932 | Fed. Rep. of Germany | 128/837 |
| 21588 | of 1897 | United Kingdom | 128/837 |
| 260600 | 10/1926 | United Kingdom | 128/832 |
| 81/02389 | 9/1981 | World Int. Prop. O. | 128/841 |

Primary Examiner—Robert A. Hafer
Assistant Examiner—Kevin G. Rooney
Attorney, Agent, or Firm—Michael G. Petit

[57] ABSTRACT

A porous pouch or pad-retaining means in a vaginal diaphragm or a cervical cap, specially designed to securely and removably house a foam pad which pad will dispense Nonoxynol-9 or other spermatostatic/lymphocytostatic chemicals where the chemicals will exert maximal effect during hydrostatic pressure changes occurring during intercourse.

4 Claims, 1 Drawing Sheet

VAGINAL DIAPHRAGMS WITH MEDICAMENT DISPENSING FOAM PADS

CROSS-REFERENCE TO RELATED APPLICATIONS

This is a continuation of application Ser. No. 07/234,812, filed Aug. 22, 1988, abandoned.

BACKGROUND OF THE INVENTION

1. Field of the Invention

This invention relates to an improved intravaginal contraceptive barrier that permits additional versatile protection against sexually transmitted disease.

2. Description of the Prior Art

Cervical caps have been used since 1350 B.C. to prevent pregnacy. Egyptians used hollowed out lemons cut in half for this purpose and squeezed out some of the juice to act as spermicide. Since the invention of latex in the 1920's, vaginal diaphragms have been used for the same purpose. In recent years, "spermicides", such as Nonoxynol-9, have been used as adjuncts to increase the efficiency of diaphragms in preventing pregnancy, as well as sexually transmitted diseases. Nonoxynol-9 (U.S. Pat. No. 2,313,477), in low non-toxic, non-cytocidal concentrations, not only increases the effectiveness of diagragms in preventing pregnancy, but also has been found to prevent cell to cell infection with AIDS viruses carried by migrant lymphocytes in semen and in endocervical secretions.

Dunn et al (U.S. Pat. No. 4,589,880) reviews the various diaphragms currently in commercial use and claims a disposable spermicide-releasing diaphragm and cervical cap. The spermicide, Nonoxynol-9, is released in situ by diffusion when a water soluble polymer matrix dissolves. The device consists of a thermoplastic elastomer such as a polyether-polyurethane that has been blended homogeneously with Nonoxynol-9, and a water soluble polymer such as polyethylene glycol. The Nonoxynol-9 and the water soluble polymer migrate to the surface of the device by diffusion and are released into the vagina at a controlled rate upon contact with vaginal fluid. The spermicide is released randomly from the surface of the device and is distributed more or less homogeneously throughout the vagina.

It is now known that the most probable place for the AIDS virus (HIV) to enter a femal upon contact with infected semen is in the vicinity of the external OS of the cervix uteri. Only on the endocervix is the epithelium thin enough to permit passage of an infected lymhocyte. Thus, the Dunn device would not concentrate Nonoxynol-9 in the area where it would be the most effective in protecting the woman against infection by HIV. In addition, the device would not be useful for women allergic or sensitive to polyurethane. Finally, the device is expected to be expensive on a per-use basis inasmuch as it is not reusable.

Gutnick, in U.S. Pat. No. 4,332,243, teaches the use of a burstable medication-releasing well in the wall of a condom or diaphragm. Gutnick's device depends upon the rupture of a partitioning membrane on the well to release medicament and is, therefore, non-reusable. Moreover, it is unclear how such a well could be refilled by a user even if such a device was reusable.

U.S. Pat. Nos. 4,332,243 and 4,393,871 describe methods for dispersing spermicides from receptacles, such as polyethylene sponges, but provide no stable anchoring mechanisms for holding such receptacles in place near the opening of the female cervix. The contraceptive sponge, although molded as if to fit the cervix, seems to wander and often turn upside/down. The concept of Loeb-Perry, using a 1 ½ inch diameter, nonoxynol-impregnated, disposable "Diaphragm Disk" with an adhesive coating on one side sounds attractive, but it is not certain how long as latex diaphragm will be tolerant of repeated applications of the adhesive before developing leaks.

There is a clear need for a reusable intravaginal device that is effective as a contraceptive, non-allergenic, easy to insert and remove, easy to clean and, most important, capable of delivering repeated doses of a spermicide such as Nonoxynol-9 or antimicrobial agent in concentrations sufficient to prevent sperm or virus-laden cells that have penetrated the contraceptive barrier from entering the cervix.

This invention relates to an improved design for vaginal diaphragms and cervical caps. The improved diaphragm or cervical cap has either an integral pad-retaining member or pouch shaped to hold a foam pad which releases a solution containing various forms of spermostatic/lymphocytostatic chemicals directly over the vaginal opening of the female uterine cervix where their dispersion under the pumping action of sexual intercourse will be optimally effective in preventing pregnancy, as well as sexually transmitted diseases, especially virus infections carried by migrant lymphocytes. Both the pad-retaining members and pouches are designed to hold a foam pad which will gradually dispense chemicals in solution from the saturated foam pad during intercourse. The choice of pad-retainer or pouch molded into the diaphragm or cervical cap is determined by the need to control chemical dispersion from the foam pad housed within the pad-retainer or pounch will, therefor, depend on the medication being dispensed and the size and shape of the foam pad. The specifications are adaptable to standard diaphragms and cervical caps made of latex or silicone.

SUMMARY OF THE INVENTION

Retainers or pouches are described for removably housing open-cell foam sponges dispensing spermostatic/lymphocytostatic chemicals, such as Nonoxynol-9, within non-disposable contraceptive devices, especially latex or silicone vaginal diaphragms and cervical caps. The pad-retainer means is molded into a vaginal diaphragm or cervical cap, such that when the diaphragm or cervical cap is properly inserted, the outlet port of the foam pad-containing pouch or the center of the pad will directly overly the external os of the cervix. The pouch is capped with a permanently located porous or semi-permeable cover which helps control the dispersion of bio-active chemicals, such as Nonoxynol-9, released from a sponge contained within the reservoir during the act of sexual intercourse. The foam pads are designed to be filled with spermatocide and inserted in the diaphragm or integral pouch before intercourse. Dispersion of the spermatocidal chemical is facilitated by the pressure changes which occur inside the foam pad during coitus.

Outstanding features are:

1. The pad-retaining pouch or pad-retaining flange is permanently fixed in an ideal position to release spermostatic antimicrobial or lymphocytostatic medications where they are critically needed to prevent the migration of sperm into the uterus, as well as intercept virus-infected migrant lymphocytes in semen and in endocervical secretions.

2. The device is capable of dispensing bioactive chemicals, such as Nonoxynol-9, especially during coitus, repeatedly, so long as they are properly refilled.

3. The addition of a properly placed reservoir will add little to the cost of reusable contraceptive devices, such as conventional vaginal diaphragms or cervical caps, and can be expected to add significantly to the contraceptive, as well as lymphocyte interceptive efficiency of these devices.

4. The the foam pad-retaining means, whether an integrally molded flange or pouch, can be expected to have a useful life as long as that of the vaginal diaphragm or the cervical cap, e.g. 1 year or more; and are not likely to cause deterioration of the outer barrier (as might be expected from the repeated gluing on of discs) or slip away into a useless position (as often occurs with shaped or unshaped contraceptive sponges).

DETAILED DESCRIPTION OF THE PREFERRED EMBODIMENT

Figure 1:
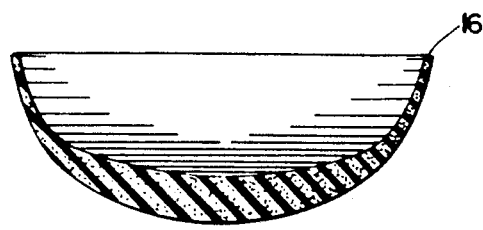
FIG. 1 A cross-sectional partial side view of a molded foam pad to be used with the contraceptive diaphragm of the present invention.
Figure 2:
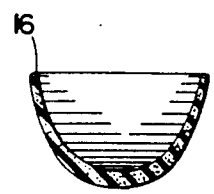
FIG. 2 A cross-sectional side view of a molded foam pad to be used with the cervical cap of the current invention.
Figure 3:
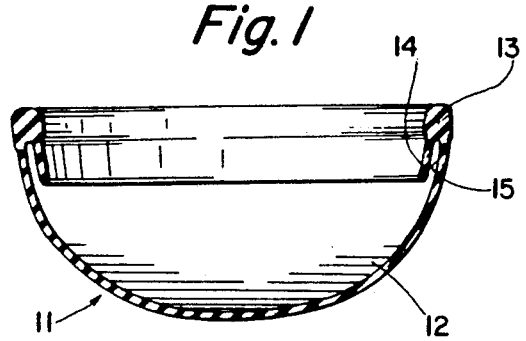
FIG. 3 FIG. 3 is a partial cross-sectional partial side view of the contraceptive diaphragm of the current invention to be used with the foam pad of FIG. 1.
Figure 4:
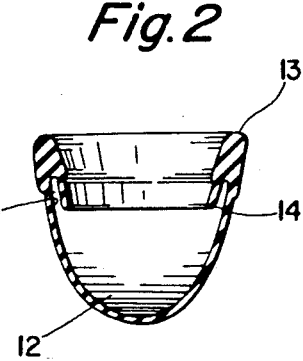
FIG. 4 FIG. 4 is a cross-sectional partial side view of the cervical cap to be used with the foam pad of FIG. 2.
Figure 5:
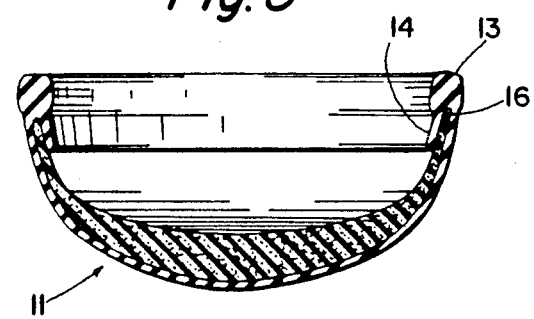
FIG. 5 FIG. 5 is a cross-sectional partial side view of the preferred embodiment of the medicament-dispensing diaphragm with the foam pad inserted within the diaphragm and held in place with a retaining flange.
Figure 6:
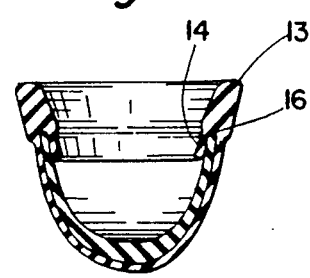
FIG. 6 FIG. 6 is a cross-sectional partial side view of the preferred embodiment of the medicament-dispensing cervical cap with the foam pad held in place by the retaining flange.

The first preferred embodiment of the present invention may be best understood by.referring to the drawings. An intravaginal diaphragm (FIG. 3) or cervical cap (FIG. 4) is molded of silicone rubber to contain an integral pad receptacle (12). The structure of the diagram and cervical cap sponge-retaining receptacles (12) are shown in cross-sectional in FIGS. 3 and 4 respectively. The diaphragm has a tensioning spring (13) and a molded silicone or latex retaining ring (14) which ring forms a notch or annular groove (15) into which the upper rim of the foam pad ((16) FIG. 1) is removably inserted by force. The curvature of the foam pad's outer surface is the same as the curvature of the inner surface of the receptacle of the diaphragm. The foam pad is held securely within the receptacle (12) of the diaphragm (11). The foam pad may be filled either by a pipette or syringe after insertion into the retaining well of the diaphragm or prior to insertion. FIGS. 5 and 6 show a foam pad retained respectively within the receptacle of a vaginal diaphragm and cervical cap by means of the integral annual flange.

Other preferred embodiments are conceptually identical to the first preferred embodiment except for the method of retaining or securing the foam pads within the receptacle and the inclusion of an outlet port.

Figure 7:
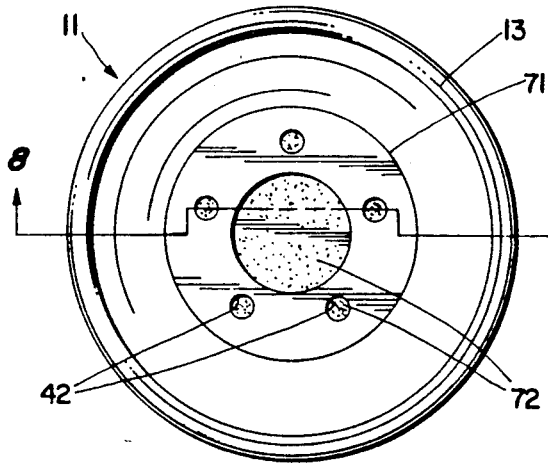
FIG. 7 FIG. 7 is a top view of a diaphragm containing a porous pouch into which a sponge may be inserted.
Figure 8:
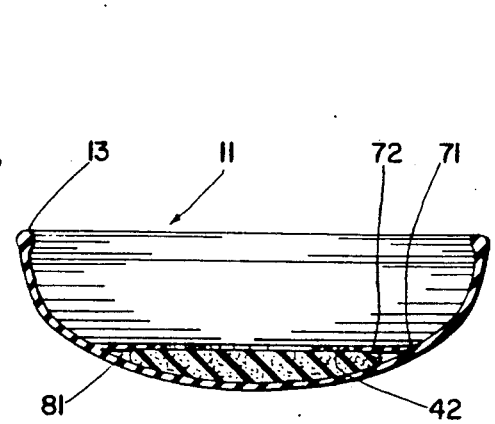
FIG. 8 FIG. 8 is a side cross-sectional view of the diaphragm of FIG. 7.

The medicament exits the reservoir through small openings (42) by diffusion aided by mechanical pumping-induced hydrostatic pressure changes that occur during coitus. FIG. 7 shows a top view of a vaginal diaphragm containing a pad-retaining pouch (71) wherein the pouch comprises a semipermeable cover through which medicament, which saturates the open cell foam pad (72) which has been placed into the pouch receptacle (81) (FIG. 8), may pass.

What is claim is:

1. A reusable intravaginal contraceptive device comprising:
   (a) a dome shaped barrier-forming member made from an elastomer which will substantially prevent sperm present on one side of said barrier-forming member from crossing said barrier forming member; and
   (b) a foam pad-retaining member permanently affixed to said barrier-forming member, said foam pad-retaining member external from the interior or cervical surface of said barrier-forming member so as to allow the release of medicament contained within a foam pad preferentially in the vicinity of the external os of the cervix uteri when said intravaginal contraceptive device is correctly positioned within the vagina; and
   (c) a medicament-dispensing open-cell foam pad, said foram being removably attached to said barrier forming member by said foam pad retaining-member thereby rendering said foam pad disposable.

2. The device claim 1 wherein said pad-retaining means is a pouch molded into said barrier-forming member.

3. The device of claim 1 wherein said medicament is Nonoxynol-9.

4. The device of claim 1 wherein said pad-retaining member is a flange molded into the interior cervix-connecting surface of said barrier-forming member.

* * * * *